United States Patent [19]

Vincent et al.

[11] Patent Number: 4,720,484
[45] Date of Patent: Jan. 19, 1988

[54] PEPTIDE COMPOUNDS HAVING A NITROGENOUS POLYCYCLIC STRUCTURE

[75] Inventors: Michel Vincent, Bagneux; Georges Remond, Versailles; Claude Cudennec, La Celle St Cloud, all of France

[73] Assignee: ADIR S.A.R.L., Neuilly-sur-Seine, France

[21] Appl. No.: 933,093

[22] Filed: Nov. 20, 1986

Related U.S. Application Data

[63] Continuation-in-part of Ser. No. 816,812, Jan. 6, 1986, abandoned.

[30] Foreign Application Priority Data

Jan. 7, 1985 [FR] France ................. 85 00140

[51] Int. Cl.⁴ .................. A61K 37/02; C07K 5/10
[52] U.S. Cl. ........................ 514/18; 530/330
[58] Field of Search ............... 514/18; 530/330

[56] References Cited

U.S. PATENT DOCUMENTS 4,353,823 10/1982 Chipens et al. .................. 530/330

Primary Examiner—Delbert R. Phillips
Attorney, Agent, or Firm—Gordon W. Hueschen

[57] ABSTRACT

The invention relates to tetrapeptide derivatives of the general formula

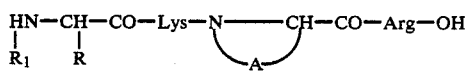

in which R represents a hydrogen atom, a straight-chain or branched alkyl radical containing from 1 to 5 carbon atoms, optionally substituted by a hydroxy, amino, mercapto, methylthio, methylsulphoxide, carboxy or guanidino group, or a benzyl or indol-3-ylmethyl radical optionally substituted by a hydroxy group, $R_1$ represents a hydrogen atom or an alkyl group containing from 1 to 4 carbon atoms,

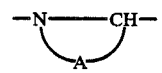

represents a nitrogenous polycyclic structure, the enantiomers, epimers and diastereoisomers thereof, as well as to the pharmaceutically acceptable acid or base addition salts thereof.

12 Claims, No Drawings

PEPTIDE COMPOUNDS HAVING A NITROGENOUS POLYCYCLIC STRUCTURE

The present application is a continuation-in-part of our prior - filed co-pending application Ser No. 816,812 filed Jan. 6, 1986, now abandoned.

The present invention relates to novel tetrapeptides, the preparation thereof, and pharmaceutical compositions containing them.

Numerous natural and synthetic tetrapeptides, and in particular tuftsine (Thr-Lys-Pro-Arg), which modify biologicial response, are known. Certain analogues of tuftsine have been described in particular in U.S. Pat. No. 4,353,823 and DE Patent No. 2,343,034, and these analogues have an activity stimulating phagocytosis that is generally comparable to that of tuftsine.

The applicants have now discovered novel tetrapeptides of which the immunomodulatory properties are superior to those of tuftsine.

More specifically, the invention relates to tetrapeptide compounds of the general formula $$R_1-HN-CH(R)-CO-Lys-N\underset{A}{\frown}CH-CO-Arg-OH \qquad I$$

in which
R represents:
  a hydrogen atom,
  a straight-chain or branched alkyl radical containing from 1 to 5 carbon atoms, optionally substituted by a hydroxy, amino, mercapto, methylthio, methylsulphoxide, carboxy or guanidino group, or
  a benzyl or indol-3-ylmethyl radical optionally substituted by a hydroxy group,
$R_1$ represents a hydrogen atom or an alkyl group containing from 1 to 4 carbon atoms.
Lys and Arg represent, respectively, the lysyl and arginyl residues linked through the peptide bonds.

$$-N\underset{A}{\frown}CH-$$

represents
a bicyclic structure of the formula:

$$\begin{array}{c} -N\phantom{xxxxx}CH- \\ (CH_2)_m\phantom{xx}(CH_2)_n \\ R_a-C-(CH_2)_p-C-R_b \\ B \end{array}$$

wherein
m represents 1 or 0,
n and p each represents 0, 1 or 2,
$R_a$ and $R_b$ each represents a hydrogen atom or may together form a direct bond when p=0,
B represents an alkylene chain $(CH_2)_q$ in which q represents 2, 3 or 4, or an unsaturated structure $(-CH=CH-)_2$ when p =0 and $R_a$ and $R_b$ together form a bond,
with the proviso that the sum of m, n, p and q is an integer of from 3 to 6, or,
1,2,3,4-tetrahydro-β-carboline the enantiomers, epimers and diastereoisomers thereof, as well as the pharmaceutically acceptable acid or base addition salts thereof.

The compounds of the formula I that are preferred are those in which the cyclic structure $$-N\underset{A}{\frown}CH-$$

represents indoline, isoindoline, tetrahydroquinoline, tetrahydroisoquinoline, perhydroindole, perhydroisoindole, perhydroisoquinoline, perhydroquinoline, perhydrocyclopenta[b]pyrrole, 2-azabicyclo[2,2,2]octane, 2-azabicyclo[2,2,1]heptane, and 1,2,3,4-tetrahydro-β-carboline.

Among the acids which may be added to compounds of the formula I to form an addition salt there may be mentioned by way of example, hydrochloric, sulphuric, phosphoric, tartaric, malic, maleic, fumaric, oxalic, methanesulphonic, ethanesulphonic, camphoric and citric acid, etc. . . .

As bases capable of forming salts with compounds of the formula I there may be used sodium, potassium, calcium or aluminium hydroxides, alkali metal or alkaline earth metal carbonates, or organic bases such as triethylamine, benzylamine, diethanolamine, tert.-butylamine, dicyclohexylamine and arginine etc. . . .

The invention relates also to a process for obtaining compounds of the formula I, characterised in that the amine function of a derivative of the formula II $$HN\underset{A}{\frown}CH-COOH \qquad II$$

in which A, together with the carbon and nitrogen atoms to which it is attached, has the same meanings as in formula I, is protected by a tert.-butoxycarbonyl radical (tBoc) by the action of di-tert.-butyl carbonate, resulting in a derivative of the formula III $$tBoc-N\underset{A}{\frown}CH-COOH \qquad III$$

in which A, together with the carbon and nitrogen atoms to which it is attached, has the same meanings as in formula I, which is condensed with methyl $N_\omega$-nitroarginate (Arg(NO$_2$)OCH$_3$) to form a derivative of the formula IV $$tBoc-N\underset{A}{\frown}CH-CO-Arg(NO_2)OCH_3 \qquad IV$$

in which A, together with the carbon and nitrogen atoms to which it is attached, has the same meanings as in formula I, from which the protecting group is then removed by trifluoroacetic acid to form a derivative of the formula V:

$$HN\underset{A}{\frown}CH-CO-Arg(NO_2)OCH_3 \qquad V$$

in which A, together with the carbon and nitrogen atoms to which it is attached, has the same meanings as in formula I, which is then condensed with N-tert.-butoxycarbonyl-$N_\omega$-benzyloxycarbonyllysine or (tBoc)Lys(Z) to form a compound of the formula VI

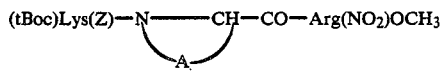   VI in which A, together with the carbon and nitrogen atoms to which it is attached, has the same meanings as in formula I, which is subjected to the action of trifluoroacetic acid and converted into a derivative of the formula VII

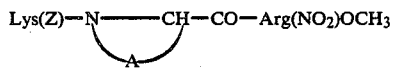   VII in which A, together with the carbon and nitrogen atoms to which it is attached, has the same meanings as in formula I, which is condensed with a derivative of the formula VIII

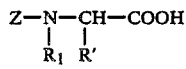   VIII in which
Z represents a protecting qroup for amine functions, especially a benzyloxycarbonyl group,
$R_1$ has the same meaning as in formula I,
R' represents a hydrogen atom, a benzyl or indol-3-ylmethyl radical optionally substituted by a hydroxy group, or a straight-chain or branched alkyl radical containing from 1 to 5 carbon atoms that is optionally substituted by a hydroxy, mercapto, methylthio, or N-nitro- or N,N-bisbenzyloxycarbonylguanidino group or by a benzyl carboxylate group to yield a derivative of the formula IX

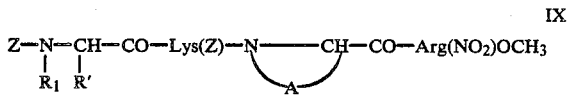   IX in which A, together with the carbon and nitrogen atoms to which it is attached, and $R_1$ have the same meanings as in formula I, and R' has the same meanings as in formula VIII, which is hydrolysed to form a derivative of the formula X

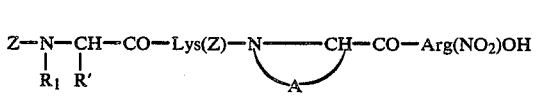   X in which A, together with the carbon and nitrogen atoms to which it is attached, and $R_1$ have the same meanings as in formula I, and R' has the same meanings as in formula VIII, from which th protecting groups are then removed by hydrogenolysis in a polar acid ic solvent in the presence of a hydrogenation catalyst, to form a derivative of the formula I which can then, I desired:

be converted into a salt by a pharmaceutically acceptable acid or base, be separated into its isomers, then, if necessary, converted into a salt by a pharmaceutically acceptable acid or base.

The derivatives of the formula IX and X are novel and the invention relates to these as well as to the derivatives of the formula I, of which they constitute intermediates in the synthesis.

The compounds of the formula I possess interesting pharmacological properties.

In particular, they stimulate the phagocytic activity of macrophages and increase the activity of "spontaneous killer" (Natural Killer NK) cells. Administered to mice with a melanoma, they inhibit to a large extent the growth of this melanoma. They assure promotion of the immune defences in animals infected by pathogenic bacterial strains.

These activities are associated with the immunomodulatory properties of the compounds of the invention, which are used therapeutically in the treatment of animals and humans suffering from cancer, diseases of viral, bacterial or fungal origin, autoimmune diseases, such as lupus erythematosus or rheumatoid arthritis, and, more generally, diseases resulting from a decrease or disturbance in the natural immune responses of the human or animal organism.

The invention relates also to pharmaceutical compositions containing at least one compound of the general formula I, or a pharmaceutically acceptable base or acid addition salt thereof, alone or in combination with one or more pharmaceutically acceptable non-toxic inert excipients or vehicles.

Of the pharmaceutical compositions according to the invention there may be mentioned more especially those which are suitable for parenteral, per- or transcutaneous, nasal, ocular or respiratory administration, and in particular injectable preparations, aerosols, eye or nose drops, creams, ointments and skin gels etc.

The dosage used varies according to the age and weight of the patient, the route of administration, the nature of the therapeutic indication and any associated treatments, and ranges from 1 microgram to 1 gram per dose or per application.

The following Examples illustrate the invention and do not limit it in any way.

The starting materials are known from the literature.

The melting points indicated are measured in accordance with the micro-Kofler technique. The $^{13}C$ nuclear magnetic resonance spectra were recorded using $D_2O$ as solvent and TMS as internal reference, and $^1H$ NMR spectra were generally recorded using $CDCl_3$ as solvent. The mass spectra are recorded after chemical ionisation (reactor gas $NH_3$) and detection by a quadrupole.

EXAMPLE 1

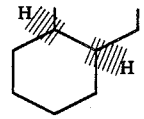

For convenience, the grouping (2S,3aS,7aS)-2-carbonylperhydroindole will be designated (S)PHI.

STAGE A:

tBoc(S)PHI-OH or [(1-tert.-butoxycarbonyl)-(2S,3aS,7aS)-perhydroindol-2-yl]carboxylic acid In a mixture of 60 cm$^3$ of dioxan and 30 cm$^3$ of water dissolve 0.03 mol of (S)PHI-OH, obtained in accordance with Tetrahedron Letters 23, (16) 1677–1680 (1982), cool to 0° C., add 70 cm$^3$ of N sodium hydroxide solution, then, drop by drop, a solution of 0.03 mol of di-tert.-butyl carbonate in 100 cm$^3$ of dioxan. Agitate for 30 minutes at a temperature of from 0° C. to 5° C., then for 2 hours at room temperature.

Evaporate the solvents under reduced pressure. Take up the residue with water acidified by citric acid to a pH of 4 and extract the aqueous phase with ethyl acetate.

Wash the organic phase with 10% aqueous sodium chloride solution, dry over anhydrous calcium sulphate, filter, and concentrate under reduced pressure. Crystallise the residue in n-pentane, suction-filter and dry.

tBoc(S)PHI-OH is obtained; m.p.=134° C.; yield: 82.5%.

IR spectrum data: $\nu$OH: 2400–3200 cm$^{-1}$; $\nu$CO (acid): 1750 cm$^{-1}$; $\nu$CO

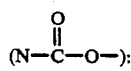

1630 cm$^{-1}$.

STAGE B tBoc(S)PHI-(S)Arg(NO$_2$)OCH$_3$

Using the method according to W. KONIG and R. GEIGER (Ber., 103, 788 (1970)), couple 0.004 mol of tBoc(S)PHI-OH obtained in the preceding stage with 0.004 mol of methyl (S)-N$_\omega$-nitroarginate using anhydrous diethylformamide as solvent.

tBoc(S)PHI-(S)Arg(NO$_2$)OCH$_3$ is obtained in a yield of 92.5% in the form of an oil which is used as such as in the following stage:

IR spectrum data: $\nu$NH: 3100–3500 cm$^{-1}$; $\nu$CO (ester): 1740 cm$^{-1}$; $\nu$CO (amide and

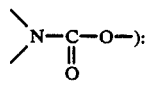

1530 and 1670 cm$^{-1}$.

STAGE C

(S)PHI(S)Arg(NO$_2$)OCH$_3$

Using the method of removing protecting groups by trifluoroacetic acid in anhydrous methylene chloride described by B. GUTTE and R. B. MERRIFIELD (J. Am. Chem. Soc., 91, 501 (1969)) there is obtained quantitatively, from 0.00352 mol of tBoc(S)PHI-(S)Arg-(NO$_2$)OCH$_3$ prepared in the preceding stage, (S)PHI-(S)Arg (NO$_2$)OCH$_3$ in the form of its trifluoroacetate, the purity of which is confirmed by thin layer chromatography (solvent: CH$_2$Cl$_2$/MeOH=9:1; R$_f$=0.1).

STAGE D tBOC(S)Lys(Z)-(S)PHI-(S)Arg(NO$_2$)OCH$_3$

By replacing in the preceding stage B tBoc(S)PHI-OH by N-tert.-butoxycarbonyl-N$_\omega$-benzyloxycarbonyl-lysine (or tBoc(S)Lys(Z)) (0.0032 mol), and (S)Arg-(NO$_2$)OCH$_3$ by (S)PHI-(S)Arg(NO$_2$)OCH$_3$ (0.0032 mol) prepared in the preceding stage, there is obtained in the same manner tBoc(S)Lys(Z)-(S)PHI-(S)Arg-(NO$_2$)OCH$_3$ in a yield of 64%.

Principal data of $^1$H NMR: 3.7 ppm: 3H(OCH$_3$); 5.1 ppm: 2H(benzyl); 7.35 ppm: 5H (aromatic); 7.8 ppm: 6H (exchangeable).

STAGE E

(S)Lys(Z)-(S)PHI-(S)Arg(NO$_2$)OCH$_3$

By removing the protecting group from tBoc(S)Lys-(S)PHI-(S)Arg(NO$_2$)OCH$_3$ by trifluoroacetic acid in the manner indicated in the preceding stage C, there is obtained quantitatively (S)Lys(Z)-(S)PHI-(S)Arg(NO$_2$)OCH$_3$ in the form of its trifluoroacetate, the purity of which is confirmed by thin layer chromatography (solvent=CH$_2$Cl$_2$/MeOH=9:1).

STAGE F

(S)(Z)Thr-(S)Lys(Z)-(S)PHI-(S)Arg(NO$_2$)OCH$_3$

By condensing (S)Lys(Z)-(S)PHI-(S)Arg(NO$_2$)OCH$_3$ with (S)-N-benzyloxycarbonylthreonine (or (S)(Z)Thr-OH) in accordance with the method indicated in the preceding stage B, there is obtained in the same manner (S) (Z)Thr-(S)Lys(Z)-(S)PHI-(S)Arg-(NO$_2$)OCH$_3$, which is purified by chromatography on silica (60–230 mesh) using as eluant a mixture of CH$_2$Cl$_2$ and MeOH (95:5). Yield: 67%.

Percentage analysis:

|  | % C | % H | % N |
| --- | --- | --- | --- |
| Calculated | 57.20 | 6.74 | 14.29 |
| Found | 57.09 | 6.69 | 14.16 |

Spectrum data: IR: $\nu$NH,OH: 2700–3600 cm$^{-1}$. $\nu$CO (amide): 1630–1720 cm$^{-1}$.

$^1$H NMR: 2.9 to 5.6 ppm: 10 H (CH and CH$_2$); 3.75 ppm: 3H (OCH$_3$); 5.1 ppm: 4H (benzylic); 7.35 ppm: 10H (aromatic).

STAGE G

(S) (Z)Thr-(S)Lys(Z)-(S)PHI-(S)Arg(NO$_2$)OH

Into a mixture of 0.6 cm$^3$ of 1N NaOH, 6 cm$^3$ of water and 20 cm$^3$ of ethanol introduce 0.0006 mol of (S)(Z)Thr-(S)Lys(Z)-(S)PHI-(S)Arg(NO$_2$)OCH$_3$ and maintain at room temperature for 5 hours. Concentrate the solution under reduced pressure, take up in water and acidify with hydrochloric acid to a pH of 2. Extract with ethyl acetate. The organic phase removed is dried over anhydrous calcium sulphate, filtered, and concentrated to dryness.

The product obtained is purified by chromatography on silica F 254 (eluant CH$_2$Cl$_2$ (MeOH: 80/20) (yield: 27%).

STAGE H

(S) Thr-(S)Lys-(S)PHI-(S)Arg-OH

Subject 0.0004 mol of (S) (Z)Thr-(S)Lys(Z)-(S)PHI-(S)Arg(NO$_2$)OH obtained in the preceding stage to catalytic hydrogenation in 25 cm$^3$ of acetic acid under a hydrogen pressure of 3 kg/cm$^2$ in the presence of 300 mg of 10% palladium-on-carbon. After evaporation of the solvent under reduced pressure the amorphous residue is taken up in 5 cm$^3$ of distilled water and separated by microfiltration.

The diacetate of (S)Thr-(S)Lys-(S)PHI-(S)ArgOH is obtained (yield 90%), which is purified if necessary by high performance preparative chromatography (phase: SiO$_2$-C$_8$ Lichoprep -RP$_8$ Merck No. 9324; eluant H$_2$O/methanol=8:2+0.02 acetic acid (yield 60%)), and lyophilised.

Spectrum data: IR: $\nu$NH and OH: 2300-3600 cm$^{-1}$; $\nu$C=O: 1570-1760 cm$^{-1}$.

NMR ($^1$H): solvent CDCl$_3$; 0.8 to 2.3 ppm: 22H (CH$_2$ and CH)+6H (CH$_3$ of CH$_3$COOH); 2.5 to 4.5 ppm: 12H (CH$_2$ and CH $\alpha$ to CO, <N, —O—); 5.5 ppm: 14H (exchangeable).

EXAMPLE 2

Gly-(S)Lys-(S)PHI-(S)Arg-OH

By replacing (S)-N-benzyloxycarbonylthreonine in Example 1, stage F, by N-benzyloxycarbonylglycine or (Z)Gly there are obtained in succession, in the same manner:

(Z)Gly-(S)Lys(Z)-(S)PHI-(S)Arg(NO$_2$)OCH$_3$ (yield 70%);

(Z)Gly-(S)Lys(Z)-(S) PHI-(S)Arg(NO$_2$)OH;

Gly-(S)Lys-(S)PHI-(S)Arg-OH (yield 98%), which is lyophilised in the form of its diacetate.

Data of $^{13}$C NMR spectrum: 43.3 ppm: CH$_2$ (Gly); 54.1 ppm: CH$_\alpha$ (Lys); 57.3 ppm: CH$_\alpha$ (Arg); 63.7 ppm: CH$_\alpha$ (PHI).

EXAMPLE 3

(S)NVa-(S)Lys-(S)PHI-(S)Arg-OH

By replacing (S)-N-benzyloxycarbonylthreonine in Example 1, stage F, by (S)-N-benzyloxycarbonylnorvaline or (S) (Z)NVa, there are obtained in succession, in the same manner:

(S) (Z)Na-(S)Lys(Z)-(S)PHI-(S)Arg(NO$_2$)OCH$_3$ (yield 61%);

(S) (Z)NVa-(S)Lys(Z)-(S)PHI-(8)Arg(NO$_2$)-OH;

(S) NVa-(S)Lys-(S)PHI-(S)Arg-OH(yield 95%), which is lyophilised in the form of its diacetate.

Data of $^{13}$C NMR spectrum: 53.8 ppm: CH$_\alpha$ (Lys); 55.3 ppm: CH$_\alpha$ (NVa); 57.2 ppm: CH$_\alpha$ (Arg); 63.4 ppm: CH$_\alpha$ (PHI).

EXAMPLES 4 to 7

In the same manner, by replacing (S)-N-benzyloxycarbonylthreonine in Example 1, stage F, by (S)-N-benzyloxycarbonylcysteine, benzyl, (S)-N-benzyloxycarbonlglutamate, (S)-N-benzyloxycarbonylphenylalanine, and (R)-N-benzyloxyalanine, there are obtained, respectively, the following compounds:

EXAMPLE 4

(S)Cys-(S)Lys-(S)PHI-(S)Arg-OH lyophilised in the form of its diacetate (yield 78%).

EXAMPLE 5

(S)Glu-(S)Lys-(S)PHI-(S)Arg-OH yield 92%, lyophilised in the form of its monoacetate. Principal characteristic fragments in mass spectrometry: m/Z: 565, 547, 523, 505, 391, 115.

EXAMPLE 6

(S)Phe-(S)Lys-(S)PHI-(S)Arg-OH yield 94%, lyophilised in the form of its diacetate.

Data of $^{13}$C NMR spectrum: 56.6 ppm: CH$_\alpha$ (Phe); 53.2 ppm: CH$_\alpha$ (Lys); 63.4 ppm: CH$_\alpha$ (PHI); 57.3 ppm: CH$_\alpha$ (Arg).

EXAMPLE 7

(R)Ala-(S)Lys-(S)PHI-(S)Arg-OH lyophilised in the form of its diacetate yield 91%).

Data of $^{13}$C NMR spectrum: 51.5 ppm: CH$_\alpha$ (Ala); 54.0 ppm: CH$_\alpha$ (Lys); 57.3 ppm: CH$_\alpha$ (Arg); 63.5 ppm: CH$_\alpha$ (PHI).

EXAMPLE 8

(S)Thr—(S)Lys—N—CH—CO—Arg—OH

The radical (S)-3-carbonyl-2-azabicyclo[2,2,2]octane shall hereinafter be designated (S)ABO.

By replacing (S) PHI-OH in Example 1, stage A, by (S)ABO-OH, prepared in accordance with the method described in European Pat. No. 51020, there are obtained in the same manner the following compounds:

STAGE A: tBoc (S)ABO-OH Yield 75%; m.p.: 200° C.

Percentage analysis:

|  | % C | % H | % N |
|---|---|---|---|
| calculated | 61.16 | 8.29 | 5.44 |
| found | 60.85 | 8.35 | 5.53 |

STAGE B: tBoc(S)ABO-(B)Arg(NO$_2$)OCH$_3$;

STAGE C: (S)ABO-(S)Arg(NO$_2$)OCH$_3$;

STAGE D: (S)tBocLys(Z)-(S)ABO-(S)Arg(NO$_2$)OCH$_3$, yield 70%;

STAGE E: (S)Lys(Z)-(B)Arg(NO$_2$)OCH$_3$,

STAGE F: (S)(Z)Thr-(S)Lys(Z)-(S)ABO-(S)Arg(NO$_2$)OCH$_3$, yield 39%;

Spectrum data: IR: $\nu$(NH,OH): 3000-3600 cm$^{-1}$; $\nu$(C=O): 1600-1710 cm$^{-1}$; $\nu$

(C—NH):

1530 cm$^{-1}$.

NMR ($^1$H): 2.9 to 3.5 ppm: 4H (N—CH$_2$); 3.7 ppm: 3H (OCH$_3$); 3.8 to 6 ppm: 5H ($\alpha$ to CO, <N); 5.1 ppm: 4H (benzylic); 2.5; 4; 6.2; 7.5 ppm: exchangeable protons (OH and NH).

STAGE G: (S) (Z)Thr-(S)Lys(Z)-(S)ABO-(S)Arg (NO$_2$)OH

STAGE H: (S)Thr-(S)Lys-(S)ABO-(S)Arg-OH in the form of its diacetate, yield 50%;

Data of $^1$NMR spectrum (solvent=D$_2$O): 1 to 2.5 ppm: 28H; 2.7 to 3.5 ppm: 4H (<N-CH$_2$) and 1H<-CH—N>; 3.5 to 5 ppm: 5H (CH $\alpha$ to 0, CO, —N>).

EXAMPLE 9

Gly-(S)Lys-(S)ABO-(S)Arg-OH

By replacing (S) (Z)Thr-OH in Example 8, stage F, by (Z)Gly-OH, there are obtained in succession, in the same manner:

(Z)Gly-(S)Lys(Z)-(S)ABO-(S)Arg(NO$_2$)OCH$_3$ yield 51%;

(Z)Gly-(S)Lys(Z)-(S)ABO-(S)Arg(NO$_2$)OH yield 91%;

Gly-(S)-Lys(S)ABO-(S)Arg-OH yield 92% (diacetate).

Data of $^{13}$C NMR spectrum: 43.4 ppm: CH$_2$ (Gly); 53.0 ppm: CH$_\alpha$ (Lys); 57.3 ppm: CH$_\alpha$ (Arg); 64.2 ppm: CH$_\alpha$ (ABO).

EXAMPLE 10

(S)NVa-(S)Lys-(S)ABO-(S)Arg-OH

By replacing (S)(Z)Thr-OH in Example 8, stage F, by (S)(Z)NVa-OH, there are obtained in succession:

(S)(Z)NVa-(S)Lys(Z)-(S)ABO-(S)Arg(NO$_2$)OCH$_3$ yield 51%;

(S)(Z)NVa-(S)Lys(Z)-(S)ABO-(S)Arg(NO$_2$)OH yield 88%;

(S)Na-(S)Lys-(S)ABO-(S)Arg-OH yield 92% (diacetate).

Data of $^{13}$C NMR spectrum; 52.7 ppm: CH$_\alpha$ (Lys); 55.5 ppm: CH$_\alpha$ (NVa); 57.2 ppm: CH$_\alpha$ (Arg); 64.0 ppm: CH$_\alpha$ (ABO).

EXAMPLES 11 TO 14

By proceeding as indicated in Example 8, stage F and replacing (S)-N-benzyloxycarbonylthreonine by (S)-N-benzyloxycarbonyltryptophan, (S)-N,N-bis-benzyloxycarbonylarginine, N,N'-bis-benzyloxycarbonyllysine and N-benzyloxycarbonylsarcosine, the following compounds are obtained in the same manner:

EXAMPLE 11

(S)Trp-(S)Lys-(S)ABO-(S)Arg-OH lyophilised in the form of its diacetate yield 89%

Data of $^{13}$C NMR spectrum: 52.1 ppm: CH$_\alpha$ (Lys); 56.1 ppm: CH$_\alpha$ (Trp); 57.2 ppm: CH$_\alpha$ (Arg); 63.8 ppm: CH$_\alpha$ (ABO).

EXAMPLE 12

(S)Arg-(S)Lys-(S)ABO-(S)Arg-OH lyophilised in the form of its tetraacetate, yield 94%

Data of $^{13}$C NMR spectrum: 53.2 ppm: CH$_\alpha$ (Lys); 55.2 ppm: CH$_\alpha$ (Arg); 57.2 ppm: CH$_\alpha$ (Arg); 63.7 ppm: CH$_\alpha$ (ABO).

EXAMPLE 13

(S)Lys)-(S)Lys-(S)ABO-(S)Arg-OH lyophilised in the form of its triacetate, yield 92%

Data of $^{13}$C NMR spectrum: 53.1 ppm: CH$_\alpha$ (Lys); 55.4 ppm: CH$_\alpha$ (Lys); 57.3 ppm: CH$_\alpha$ (Arg); 64.1 ppm: CH$_\alpha$ (ABO).

EXAMPLE 14

Sar-(S)Lys-(S)ABO-(S)Arg-OH lyophilised in the form of its diacetate, yield 97%

Principal characteristic fragments in mass spectrometry: m/Z: 511, 493, 451, 115, 110.

EXAMPLE 15

Gly-(S)Lys-(S)IND-(S)Arg-OH

By proceeding as in Example 2, but replacing (S)PHI-OH in stage A by (S)-2-carboxyindoline or (S) IND-OH, there is obtained in the same manner Gly-(S)Lys-(S)IND-(S)Arg-OH in the form of its diacetate.

Principal characteristic fragments in mass spectrometry: m/Z: 487, 445, 302, 274, 260, 242, 186, 168, 118, 115.

EXAMPLES 16 TO 19

In the same manner, using (S)-1-carboxyisoindoline or (S)ISI, 3-carboxy-2-azabicyclo[2,2,1]heptane or ABH-OH, (S) -3-carboxy-1,2,3,4-tetrahydro-β-carboline or (S)THC-OH, and 1-carboxyperhydroisoindole or PHII-OH, the following compounds are obtained:

EXAMPLE 16

Gly-(S)Lys-(S)ISI-Arg-OH lyophilised in the form of its diacetate, yield 91%

Principal characteristic fragments in mass spectrometry: m/Z=487, 445, 302, 274, 260, 186, 168, 118, 115.

EXAMPLE 17

Gly-(S)Lys-ABH-(S)Arg-OH lyophilised in the form of its diacetate, yield 94%

Principal characteristic fragments in mass spectrometry: m/Z=483, 465, 441, 423.

EXAMPLE 18

Gly-(S)Lys-(S)THC-(S)Arg-OH obtained in the form of its diacetate, yield 90%

Principal characteristic fragments in mass spectrometry: m/Z=498, 313, 186, 115.

EXAMPLE 19 Gly-(S)Lys-PHII-(S)Arg-OH lyophilised in the form of its diacetate, yield 95%

Principal characteristic fragments in mass spectrometry: m/Z=493, 451, 280, 266, 186, 129, 115.

EXAMPLES 20 AND 21

By proceed ing as ind icated in Example 3 and replacing (S)PHI-OH by 3-carboxyperhydroisoquinoline (or PHIQ-OH) and 2-carboxyperhyd rocyclopenta[b]pyrrole (or PCP-OH), the compounds of the following Examples are obtained:

EXAMPLE 20

(S)NVa-(S)Lys-PHIQ-(S)Arg-OH lyophilised in the form of its diacetate, (yield 96%)

Principal characteristic fragments in mass spectrometry: m/Z=550, 549, 508, 507, 393, 375, 228, 138, 115, 100.

EXAMPLE 21

(S)NVa- (S)Lys-PCP-Arg-OH lyophilised in the form of its diacetate, (yield 94%)

EXAMPLE 22

(S)Thr-(S)Lys-(S)PCP-(S)Arg-OH

By replacing (S)PHI-OH in Example 1, stage A, by (S)PCH-OH, in the same manner (S)Thr-(S)Lys-(S)PCP-(S)Arg-OH is obtained in the form of its diacetate. Principal characteristic fragments in mass spectrometry: m/Z=481, 463, 455, 437, 419.

EXAMPLE 23

S(Leu)-(S)Lys-THQ-(S)Arg-OH

By proceeding as indicated in Example 1, but replacing in stage A (S)PHI-OH by 2-carboxy-1,2,3,4-tetrahdroquinoline or THQ-OH, and, in stage F, (S) (Z)Thr-OH by (S)-N-benzyloxycarbonylleucine, (S)Leu-(S)Lys-THQ-(S)Arg-OH is obtained.

EXAMPLE 24

S(Lys)-(S)Lys-PHQ-(S)Arg-OH

By proceeding as before, but using in stage A 2-carboxyperhydroquinoline (PHQ-OH) and, in stage F, N, $N_\omega$-bis-benzyloxycarbonyllysine, (S)Lys-(S)Lys-PHQ-(S)Arg-OH is obtained.

EXAMPLE 25

Gly-(S Lys-PHQ-(S)Arg-OH

By replacing (S) PHI-OH in stage A of Example 2 by PHQ-OH, Gly-(S)Lys-PHQ-(S)Arg-OH is obtained in the form of its diacetate.

Principal characteristic fragments in mass spectrometry: m/Z=525, 507, 483, 465, 138, 115.

EXAMPLE 26

S (Met)-(S)Lys-(S)THIQ-(S)Arg-OH

By proceeding as before and using in stage A (S)-3-carboxy-1,2,3,4-tetrahydroisoquinoline or (S)THIQ-OH and, in stage F, (8)-N-benzyloxycarbonylmethionine, S(Met)-(S)Lys-(S)THIQ-(S)Arg-OH, lyophilised in the form of its diacetate, is obtained.

Principal characteristic fragments in mass spectrometry: m/Z=533, 288, 260, 274.

EXAMPLE 27

S-oxide of (S)Met-(S)Lys-(S)THIQ-(S)ARG-OH

By replacing (S)-N-benzyloxycarbonylmethionine in the preceding Example by its S-oxide, the S-oxide of (S)Met-(S)Lys-(S)THIQ-(S)Arg-OB is obtained in the form of its diacetate.

Principal characteristic fragments in mass spectrometry: m/Z=549, 288, 276, 274.

PHARMACOLOGICAL STUDY OF THE COMPOUNDS OF THE INVENTION

The capacity of the compounds of the invention to stimulate the activity of immuno-competent cells has been verified in vitro and in vivo.

EXAMPLE 28

Stimulation of phagocytosis in vitro

In vitro, the technique described by DESCAMPS B., 1980 (Ann. Immunol. Inst. Past. 131C, No. 2, p. 10) was used to measure the stimulation of the phagocytic capacities of macrophages by compounds of the invention: Petri dishes are inoculated with peritoneal macrophages of mice (strain $B_6D_2F_1$) in an amount of $10^4$ cells per dish. After inoculation of the medium with the culture, the compounds of the invention are added in aqueous solution at a concentration of 25 micromols per dish, then red corpuscles of sheep opsonized by specific immunoglobulins are introduced. After a contact time of 1 hour, the cultures are washed and the macrophages that have ingested more than 2 red corpuscles are counted.

The compounds of the invention increase by 23% the phagocytic capacity of the macrophages by comparison with control cultures. Under the same conditions, the activating ability of tuftsine is 15%.

EXAMPLE 29

Promotion of the N.K. activity

The compounds according to the invention were also tested for their abil ity to promote the "spontaneous killer" ("Natural killer") activity. The cells provided with this ability form the first line of defence of the organism vis-a-vis septic, viral or tumoral invasion.

To evaluate their stimulating ability, compounds according to the invention were examined according to the technique of REYNOLDs et. al., 1981, (J. Immunol. 127, 282).

The compounds are injected intravenously at a dose of from 20 to 50 μg/kg into mice of strain B6D2F1.

Three days after treatment, the animals are sacrificed, their spleen removed and the spleen is dissociated into its constituent cells which are used to inoculate a culture in the presence of tumoral cells YAC-1 previously labelled with radioactive chromium. At the start of incubation, the destructive capacity of the compounds of the invention is measured by the quantity of chromium liberated.

By way of example, the compound of Example 8, at a dose of 25 μg/kg, induces by comparison with a control an increase of 15% in the liberation of chromium, whilst tuftsine, at a dose of 40 μg/kg, causes a liberation of only 10%.

EXAMPLE 30

Inhibition of the growth of the melanoma B16

Melanomas are cancerous tumours sensitive to the reaction of the immune system of the patient. They thus constitute an ideal model for demonstrating any stimulation of antitumoral defence.

The compound according to Example 1 has, for example, been shown to be capable of slowing down by 40% the growth of melanoma B16 in mice when the product is administered intraperitoneally in an amount of 20 μg/kg 3 times per week. Under the same conditions, tuftsine has been shown to be incapable of promoting any slowing down in the growth of the implanted tumour.

EXAMPLE 31

Increase in the resistance of animals to infection

Certain pathogenic bacterial strains are capable of killing the healthy host into which they are inoculated. This is the case, for example, of *Klebsiella pneumoniae*, the agent responsible for pneumonia (Parant, M., et al., Proc. Natl. Acad. Sci. USA, 1978, 75, No. 7, 3395).

When the compound of Example 8 is administered at a dose of 60 μg per animal 48 hours before infection to female Swiss mice weighing from 20 to 25 g, inoculated i.p. with the strain *Klebsiella pneumoniae* 7823, a protection against death by infection of all the animals is observed. Under the same conditions, tuftsine is capable of saving only 20% of the animals.

EXAMPLES 32

Increase of the lyhocytic response to mitogens

Lectine extracts of plants are capable of serving as a substitute in vitro for the stimulation of the proliferation of lymphocytes normally induced by specific antigens. These agents are lymphocytic mitogens.

After placing lymphocytes in contact with such a mitogen it is possible to measure the intensity of the proliferation and thus to measure the immuno-protective reactivity of animals treated by a compound (Daguillard, F. Med. Clin. North Am., 56, 293).

Thus, spleen lymphocytes of mice treated with 0.5 mg/kg of the compound of Example 14 exposed to Concanaval ine A at a concentration of 0.5 mg/ml respond by a proliferation equal to 1.78 times that of lymphocytes of animals that have not been treated.

EXAMPLE 33

Pharmaceutical compositions

| Injectable solution | |
|---|---|
| Gly—(S)Lys—(S)PHI—(S)Arg—OH | 0.050 g |
| water for injectable preparation | 2 cm³ |
| Skin cream | |
| (S)Thr—(S)Lys—(S)ABO—(S)Arg—OH | 5 g |
| proplyene glycol | 25 g |
| white petroleum jelly | 10 g |
| 95% alcohol | 10 g |
| purified water qs | 100 g |

We claim:

1. A Compound of the general formula I

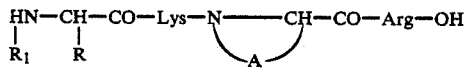

in which
R represents:
hydrogen atom,
straight-chain or branched alkyl radical containing from 1 to 5 carbon atoms, optionally substituted by a hydroxy, amino, mercapto, methylthio, methylsulphoxide, carboxy or guanidino group, or
benzyl or indol-3-ylmethyl radical optionally substituted by a hydroxy group,
$R_1$ represents a hydrogen atom or an alkyl group containing from 1 to 4 carbon atoms,
Lys and Arg represent, respectively, the lysyl and arginyl residues linked through the peptide bonds.

represents
bicyclic structure of the formula:

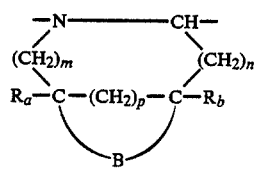

wherein
m represents 1 or 0,
n and p each represents 0, 1 or 2,
$R_a$ and $R_b$ each represents a hydrogen atom or may together form a direct bond when p=0,
B represents an alkylene chain $(CH_2)q$ in which q represents 2, 3 or 4, or an unsaturated structure $(-CH=CH-)_2$ when p=0 and $R_a$ and $R_b$ together form a bond,
with the proviso that the sum of m, n, p and q is an integer of from 3 to 6, or,
1, 2, 3, 4-tetrahydro-β-carboline the enantiomers, epimers and diastereoisomers thereof, as well as the pharmaceutically acceptable acid or base addition salts thereof.

2. A compound of claim 1 in which the cyclic structure

represents indoline, isoindoline, tetrahydroquinoline, tetrahydroisoquinoline, perhydroindole, perhydroisoindole, perhydroisoquinoline, perhydroquinoline, perhydrocyclopenta[b]pyrrole, 2-azabicyclo[2,2,2]octane, 2-azabicyclo[2,2,1]heptane, and 1,2,3,4-tetrahydro-β-carboline, the enantiomers, epimers and diastereoisomers thereof, as well as the pharmaceutically acceptable acid or base addition salts thereof.

3. A compound of claim 1 in which R represents a hydrogen atom, or a straight-chain or branched alkyl radical having from 1 to 5 carbon atoms optionally substituted by a hydroxy group, the enantiomers, epimers and diastereoisomers thereof, as well as the pharmaceutically acceptable acid or base addition salts thereof.

4. A compound of claim 1 which is (S)Thr-(S)Lys-(S)PHI-(S)Arg-OH and the pharmaceutically acceptable acid or base addition salts thereof.

5. A compound of claim 1 which is (S)Thr-(S)Lys-(S)ABO-(S)Arg-OH and the pharmaceutically acceptable acid or base addition salts thereof.

6. A compound of claim 1 which is Gly-(S)Lys-(S)PHI-(S)Arg-OH and the pharmceutically acceptable acid or base addition salts thereof.

7. A compound of claim 1 which is Gly-(S)Lys-(S)ABO-(S)Arg-OH and the pharmaceutically acceptable acid or base addition salts thereof.

8. A compound of claim 1 which is (S)NVa-(S)Lys-(S)PHI-(S)Arg-OH and the pharmaceutically acceptable acid or base addition salts thereof.

9. A compound of claim 1 which is (S)NVa-(S)Lys-(S)ABO-(S)Arg-OH and the pharmaceutically acceptable acid or base addition salts thereof.

10. A compound of claim 1 which is Sar-(S)Lys-(S)ABO-(S)Arg-OH and the pharmaceutically acceptable acid and base addition salts thereof.

11. A pharmaceutical composition suitable for treatment of immunomodulatory conditions containing an effective amount of at least one compound of claim 1 together with a suitable pharmaceutical carrier.

12. A method for treating a living animal body afflicted with a disease resulting from a decrease or disturbance in the natural immune response, comprising the step of administering to the said living animal an effective amount of a compound of claim 1 which is suitable for the alleviation of the said condition.

* * * * *

UNITED STATES PATENT AND TRADEMARK OFFICE
CERTIFICATE OF CORRECTION

PATENT NO. : 4,720,484
DATED : January 19, 1988
INVENTOR(S) : Michel Vincent, Georges Remond and Claude Cudennec It is certified that error appears in the above—identified patent and that said Letters Patent is hereby corrected as shown below:

Col. 3, line 62; "th" should read -- the --
Col. 3, line 64; "acid ic" should read -- acidic --
Col. 5, line 42; "diethylformamide" should read -- dimethylformamide --
Col. 7, line 21; "($^1$H)):" should read -- ($^1$H): --
Col. 7, line 23; "<N," should read -- >N, --
Col. 7, line 49; "(Z)Na-" should read -- (Z)NVa- --
Col. 7, line 51; "-(S)PHI-(8)Arg($NO_2$)-" should read -- -(S)PHI-(S)Arg(NO2)- --
Col. 7, lines 61&62; "(S)-N-benzyloxycarbonlglutamate," should read
  -- (S)-N-benzyloxycarbonylglutamate, --
Col. 8, line 4; after "m/Z:" insert -- 583 (invisible), --
Col. 8, line 43; "-(B)Arg($NO_2$)$OCH_3$;" should read -- -(S)Arg($NO_2$)$OCH_3$; --
Col. 8, line 47; "-(B)Arg($NO_2$)$OCH_3$," should read -- -(S)Arg($NO_2$)$OCH_3$; --
Col. 8, line 59; "<N);" should read -- >N); --
Col. 8, line 66; "$^1$NMR" should read -- $^1$H NMR --
Col. 8, line 67; "(<N-$CH_2$) and 1H<-" should read -- (>N-$CH_2$) and 1H>- --
Col. 8, line 68; "N>" both occurrences in that line should read -- N< --
Col. 9, line 57; "(S)Lys)-" should read -- (S)Lys- --
Col. 10, line 38; start a new paragraph after "EXAMPLE 19" beginning with
  "Gly-(S)Lys-"
Col. 10, line 44; "proceed ing as ind icated" should read
  -- proceeding as indicated --
Col. 10, line 46; "2-carboxyperhyd rocyclopenta[b]pyr-" should read
  -- 2-carboxyperhydrocyclopenta[b]pyr- --
Col. 11, line 6; "-tetrah-" should read -- -tetrahy- --
Col. 11, line 19; "Gly-(S Lys-" should read -- Gly-(S)Lys- --
Col. 11, line 39; "-(S)ARG-OH" should read -- -(S)Arg-OH --

UNITED STATES PATENT AND TRADEMARK OFFICE
CERTIFICATE OF CORRECTION

PATENT NO. : 4,720,484

DATED : January 19, 1988

INVENTOR(S) : Michel Vincent, Georges Remond and Claude Cudennec

It is certified that error appears in the above—identified patent and that said Letters Patent is hereby corrected as shown below:

Col. 11, line 42; "-(S)Arg-OB" should read -- -(S)Arg-OH --
Col. 12, line 10; "abil ity" should read -- ability --
Col. 12, line 66; "lyhocytic" should read -- lymphocytic --
Col. 13, line 10; "Concanaval ine" should read -- Concanavaline --
Col. 13, approximately line 23 (in Table, first column, line 6); "proplyene" should read -- propylene --
Col. 14, line 43; "pharmceutically" should read -- pharmaceutically --

Signed and Sealed this

Second Day of August, 1988

Attest:

DONALD J. QUIGG

Attesting Officer

Commissioner of Patents and Trademarks